United States Patent
Nordness et al.

(10) Patent No.: US 8,282,618 B2
(45) Date of Patent: Oct. 9, 2012

(54) DISPOSABLE BOXER BRIEF

(75) Inventors: Cynthia H. Nordness, Oshkosh, WI (US); Katherine C. Wheeler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 484 days.

(21) Appl. No.: 10/316,964

(22) Filed: Dec. 11, 2002

(65) Prior Publication Data

US 2004/0116881 A1    Jun. 17, 2004

(51) Int. Cl.
*A61F 13/15* (2006.01)
(52) U.S. Cl. .............. 604/396; 604/385.27; 604/385.01
(58) Field of Classification Search .................. 604/358, 604/385.01, 385.14, 385.27, 393–397; 2/400–408
See application file for complete search history.

(56) References Cited

U.S. PATENT DOCUMENTS

| | | |
|---|---|---|
| 478,281 A | 7/1892 | Hamilton et al. |
| 1,577,409 A | 3/1926 | Rand |
| 1,664,298 A | 3/1928 | Katz |
| 1,971,558 A | 8/1934 | Goodman |
| 2,030,306 A | 2/1936 | Lain |
| 2,032,982 A | 3/1936 | Gerstman |
| 2,088,302 A | 7/1937 | McKeever |
| 2,116,822 A | 5/1938 | Berger |
| 2,131,808 A | 10/1938 | Joa |
| 2,242,526 A | 5/1941 | Kneibler |
| 2,252,019 A | 8/1941 | Meinecke et al. |
| 2,319,138 A * | 5/1943 | Kneibler ............................ 2/234 |
| 2,391,641 A | 12/1945 | O'Hern |
| 2,435,945 A | 2/1948 | Redmond |
| 2,450,789 A | 10/1948 | Frieman |
| 2,522,510 A | 9/1950 | Fridolph |
| 2,538,596 A | 1/1951 | Sheridan |
| 2,675,806 A | 1/1954 | Bram |
| 2,711,735 A | 6/1955 | Sabo |
| 2,838,047 A | 6/1958 | Sidnell |
| 2,842,129 A | 7/1958 | Ernstorff |
| 2,859,752 A | 11/1958 | Haber |
| 3,245,407 A | 4/1966 | Mason |
| 3,338,992 A | 8/1967 | Kinney |
| 3,341,394 A | 9/1967 | Kinney |
| 3,418,660 A | 12/1968 | Shumate |
| 3,502,538 A | 3/1970 | Petersen |
| 3,502,763 A | 3/1970 | Hartmann |

(Continued)

FOREIGN PATENT DOCUMENTS

AT    168478    6/1951

(Continued)

OTHER PUBLICATIONS

Printed materials (3 pages) showing pull-on diapers disclosed at a trade show Apr. 27-29, 2004 in Miami Beach, Florida, U.S.A.

(Continued)

*Primary Examiner* — Michele M Kidwell
(74) *Attorney, Agent, or Firm* — Dority & Manning, P.A.

(57) ABSTRACT

A disposable pant includes a garment shell including a stretchable material. In one embodiment, the pant includes a front panel, a back panel and two leg panels. In another embodiment, the pant includes a middle panel and two leg panels. In another embodiment, the panel includes a single panel. The panel can include an absorbent structure either attached to, or integral with, the garment shell.

17 Claims, 9 Drawing Sheets

U.S. PATENT DOCUMENTS

| | | |
|---|---|---|
| 3,542,615 A | 11/1970 | Dobo et al. |
| 3,611,443 A | 10/1971 | Braun |
| 3,648,699 A | 3/1972 | Anderson et al. |
| 3,678,516 A | 7/1972 | Backer |
| 3,692,618 A | 9/1972 | Dorschner et al. |
| 3,714,946 A | 2/1973 | Rudes |
| 3,739,398 A | 6/1973 | Sarmiento |
| 3,802,817 A | 4/1974 | Matsuki et al. |
| 3,806,007 A | 4/1974 | Grantham |
| 3,844,282 A | 10/1974 | King |
| 3,859,667 A | 1/1975 | Roy |
| 3,869,999 A | 3/1975 | Richter |
| 3,920,237 A | 11/1975 | Grantham |
| 4,059,257 A | 11/1977 | Grantham |
| 4,081,301 A | 3/1978 | Buell |
| 4,100,324 A | 7/1978 | Anderson et al. |
| 4,106,125 A | 8/1978 | Palumbo |
| 4,114,621 A | 9/1978 | Mims, Jr. |
| 4,145,763 A | 3/1979 | Abrams et al. |
| 4,227,952 A | 10/1980 | Sabee |
| 4,280,230 A | 7/1981 | LaFleur |
| 4,284,454 A | 8/1981 | Joa |
| 4,300,241 A | 11/1981 | Shaull |
| 4,310,929 A | 1/1982 | Finlay |
| 4,327,448 A | 5/1982 | Lunt |
| 4,338,939 A | 7/1982 | Daville |
| 4,340,563 A | 7/1982 | Appel et al. |
| 4,368,565 A | 1/1983 | Schwarz |
| 4,392,259 A | 7/1983 | Bredo |
| 4,397,704 A | 8/1983 | Frick |
| 4,417,938 A | 11/1983 | Sigl |
| 4,449,254 A | 5/1984 | Fogg |
| 4,555,245 A | 11/1985 | Armbruster |
| 4,560,381 A * | 12/1985 | Southwell ............... 604/396 |
| 4,597,110 A | 7/1986 | Smith, Sr. et al. |
| 4,608,115 A | 8/1986 | Schroth et al. |
| 4,644,945 A | 2/1987 | Thorner |
| 4,646,362 A | 3/1987 | Heran et al. |
| 4,650,530 A | 3/1987 | Mahoney et al. |
| 4,655,760 A | 4/1987 | Morman et al. |
| 4,663,106 A | 5/1987 | Pomplun et al. |
| 4,663,220 A | 5/1987 | Wisneski et al. |
| 4,665,306 A | 5/1987 | Roland et al. |
| 4,671,793 A | 6/1987 | Hults et al. |
| 4,675,918 A | 6/1987 | O'Brien |
| 4,704,116 A | 11/1987 | Enloe |
| 4,745,636 A | 5/1988 | Lunt |
| 4,771,483 A | 9/1988 | Hooreman et al. |
| 4,786,346 A | 11/1988 | Ales et al. |
| 4,805,243 A * | 2/1989 | Gibbens et al. ............... 2/228 |
| 4,816,094 A | 3/1989 | Pomplun et al. |
| 4,835,795 A | 6/1989 | Lonon |
| 4,847,134 A | 7/1989 | Fahrenkrug et al. |
| 4,870,958 A | 10/1989 | Webster |
| 4,872,221 A | 10/1989 | Stone, III |
| 4,875,240 A | 10/1989 | Barrett |
| 4,883,549 A | 11/1989 | Frost et al. |
| 4,892,536 A | 1/1990 | DesMarais et al. |
| 4,895,568 A | 1/1990 | Enloe |
| 4,935,021 A | 6/1990 | Huffman et al. |
| 4,946,539 A | 8/1990 | Ales et al. |
| 4,955,880 A | 9/1990 | Rodriquez |
| 4,964,860 A | 10/1990 | Gipson et al. |
| D315,050 S | 3/1991 | Bush et al. |
| 5,014,364 A | 5/1991 | Orr |
| 5,022,240 A | 6/1991 | Peleg |
| 5,046,272 A | 9/1991 | Vogt et al. |
| 5,052,058 A | 10/1991 | Mueller |
| 5,067,178 A | 11/1991 | Katchka |
| 5,087,253 A | 2/1992 | Cooper |
| 5,103,505 A | 4/1992 | Llorens |
| 5,135,522 A | 8/1992 | Fahrenkrug et al. |
| 5,160,331 A * | 11/1992 | Forester et al. ............... 604/364 |
| 5,171,388 A | 12/1992 | Hoffman et al. |
| 5,187,817 A | 2/1993 | Zolner |
| 5,210,882 A | 5/1993 | Moretz et al. |
| 5,217,782 A | 6/1993 | Moretz et al. |
| 5,226,992 A | 7/1993 | Morman |
| D341,243 S | 11/1993 | Costella et al. |
| 5,297,296 A | 3/1994 | Moretz et al. |
| 5,303,424 A | 4/1994 | Cromartie |
| 5,306,536 A | 4/1994 | Moretz et al. |
| 5,315,716 A | 5/1994 | Baum |
| 5,315,717 A | 5/1994 | Moretz et al. |
| 5,370,634 A | 12/1994 | Ando et al. |
| 5,379,462 A | 1/1995 | Morgan et al. |
| 5,382,246 A | 1/1995 | Kawano |
| 5,435,014 A | 7/1995 | Moretz et al. |
| 5,445,628 A | 8/1995 | Gipson et al. |
| 5,500,063 A | 3/1996 | Jessup |
| 5,545,158 A | 8/1996 | Jessup |
| 5,549,593 A | 8/1996 | Ygge et al. |
| 5,554,149 A | 9/1996 | O'Donnell |
| 5,556,504 A | 9/1996 | Rajala et al. |
| 5,566,392 A | 10/1996 | Dzelzkalns |
| D377,557 S | 1/1997 | Jagger |
| 5,649,913 A | 7/1997 | Cohen |
| D382,386 S | 8/1997 | Malone |
| 5,669,902 A | 9/1997 | Sivilich |
| 5,669,996 A | 9/1997 | Jessup |
| 5,690,626 A | 11/1997 | Suzuki et al. |
| 5,690,627 A | 11/1997 | Clear et al. |
| 5,704,071 A | 1/1998 | Barclay et al. |
| 5,716,478 A | 2/1998 | Boothe et al. |
| 5,718,003 A | 2/1998 | Gwinn |
| 5,733,401 A | 3/1998 | Linman et al. |
| 5,746,730 A | 5/1998 | Suzuki et al. |
| 5,755,902 A | 5/1998 | Reynolds |
| 5,759,340 A | 6/1998 | Boothe et al. |
| 5,790,983 A | 8/1998 | Rosch et al. |
| 5,827,260 A | 10/1998 | Suzuki et al. |
| 5,853,405 A | 12/1998 | Suprise |
| 5,876,394 A | 3/1999 | Rosch et al. |
| 5,891,122 A | 4/1999 | Coates |
| D408,964 S | 5/1999 | Hernandez |
| 5,906,604 A | 5/1999 | Rönnberg et al. |
| 5,906,879 A | 5/1999 | Huntoon et al. |
| 5,907,872 A | 6/1999 | Alberts et al. |
| 5,921,974 A | 7/1999 | Kikuchi |
| 5,953,754 A | 9/1999 | Rosch et al. |
| 5,956,774 A | 9/1999 | Mackley |
| 5,978,971 A | 11/1999 | Wald |
| D417,940 S | 12/1999 | Coates et al. |
| 6,009,558 A | 1/2000 | Rosch et al. |
| 6,010,586 A | 1/2000 | Suprise |
| 6,018,822 A | 2/2000 | Hernandez |
| 6,022,443 A | 2/2000 | Rajala et al. |
| 6,105,171 A | 8/2000 | Niedermeyer |
| 6,142,983 A | 11/2000 | Suprise et al. |
| 6,145,132 A | 11/2000 | Towner |
| 6,149,637 A | 11/2000 | Allen et al. |
| 6,149,755 A | 11/2000 | McNichols et al. |
| 6,168,585 B1 | 1/2001 | Cesco-Cancian |
| 6,174,303 B1 | 1/2001 | Suprise et al. |
| 6,192,521 B1 | 2/2001 | Alberts et al. |
| 6,205,592 B1 | 3/2001 | Gouws |
| 6,248,097 B1 | 6/2001 | Beitz et al. |
| 6,287,169 B1 | 9/2001 | Willms et al. |
| 6,289,519 B1 | 9/2001 | Murakami et al. |
| 6,293,934 B1 | 9/2001 | Kumasaka |
| 6,293,936 B1 | 9/2001 | Otsubo |
| 6,293,937 B2 | 9/2001 | Matsushita et al. |
| 6,308,339 B1 | 10/2001 | Murakami et al. |
| 6,312,420 B1 | 11/2001 | Sasaki et al. |
| 6,319,347 B1 | 11/2001 | Rajala et al. |
| 6,342,050 B1 | 1/2002 | Rönnberg et al. |
| 6,368,312 B1 | 4/2002 | Otsubo |
| D456,995 S | 5/2002 | Baker |
| 6,463,591 B1 | 10/2002 | Toratani |
| 6,475,201 B2 | 11/2002 | Saito et al. |
| 6,516,473 B2 * | 2/2003 | Saito ............... 2/400 |
| 6,539,554 B1 | 4/2003 | Portela |
| 6,560,786 B2 | 5/2003 | Lipton |
| 6,585,840 B2 | 7/2003 | Rabe et al. |
| 6,626,883 B2 | 9/2003 | Wada et al. |
| 6,666,851 B2 | 12/2003 | Otsubo et al. |
| 6,807,685 B1 | 10/2004 | Hasegawa et al. |

| | | | | | | |
|---|---|---|---|---|---|---|
| 6,833,179 | B2 * | 12/2004 | May et al. ............... 428/212 | GB | 2 208 263 | 3/1989 |
| 2001/0014798 | A1 | 8/2001 | Fernfors | GB | 2 269 978 | 3/1994 |
| 2001/0044614 | A1 | 11/2001 | Damay et al. | GB | 2 269 998 | 3/1994 |
| 2002/0000291 | A1 | 1/2002 | Coenen et al. | GB | 2 269 999 | 3/1994 |
| 2002/0002021 | A1 | 1/2002 | May et al. | GB | 2 327 859 | 2/1999 |
| 2002/0002358 | A1 | 1/2002 | Durrance et al. | JP | 2000 355801 | 12/2000 |
| 2002/0009940 | A1 | 1/2002 | May et al. | JP | 2001 172801 | 6/2001 |
| 2002/0084017 | A1 | 7/2002 | Rabe et al. | JP | 2001 172802 | 6/2001 |
| 2002/0087137 | A1 | 7/2002 | Christoffel et al. | JP | 3177341 | 6/2001 |
| 2002/0099345 | A1 | 7/2002 | Saito et al. | JP | 2001 204762 | 7/2001 |
| 2003/0109842 | A1 | 6/2003 | Louis et al. | JP | 2001 204764 | 7/2001 |
| 2003/0115660 | A1 | 6/2003 | Hopkins | JP | 2001 204765 | 7/2001 |
| 2004/0098791 | A1 | 5/2004 | Faulks | JP | 3182069 | 7/2001 |
| 2004/0102746 | A1 | 5/2004 | Mortell et al. | JP | 2001 207301 | 8/2001 |
| 2004/0107481 | A1 | 6/2004 | Mortell et al. | JP | 2001 224615 | 8/2001 |

FOREIGN PATENT DOCUMENTS

| | | |
|---|---|---|
| JP | 2001 238909 | 9/2001 |
| CA | 2356510 A1 | 2/2003 |
| JP | 2001 245929 | 9/2001 |
| DE | 435 579 | 2/1927 |
| JP | 2001 248002 | 9/2001 |
| DE | 809 844 | 8/1951 |
| JP | 2001 254202 | 9/2001 |
| DE | 839 244 | 5/1952 |
| JP | 2001 262402 | 9/2001 |
| DE | 101 44 255 C1 | 2/2003 |
| JP | 3205643 | 9/2001 |
| EP | 217 032 | 4/1987 |
| JP | 3205690 | 9/2001 |
| EP | 0 717 971 | 6/1996 |
| JP | 3208258 | 9/2001 |
| EP | 763 353 | 3/1997 |
| JP | 2001 299813 | 10/2001 |
| EP | 549 988 | 6/1998 |
| JP | 3221601 | 10/2001 |
| EP | 904 758 | 3/1999 |
| JP | 2001 309946 | 11/2001 |
| EP | 911 006 | 4/1999 |
| JP | 2001 333932 | 12/2001 |
| EP | 0 925 729 A2 | 6/1999 |
| JP | 2002 095700 | 4/2002 |
| EP | 933 072 | 8/1999 |
| JP | 2002-320641 | 11/2002 |
| EP | 1 048 231 | 11/2000 |
| JP | 2004 159949 | 6/2004 |
| EP | 1 060 677 | 12/2000 |
| WO | 95/16421 | 6/1995 |
| EP | 1 060 679 | 12/2000 |
| WO | 95/18589 | 7/1995 |
| EP | 1 108 371 | 6/2001 |
| WO | 96/03950 | 2/1996 |
| EP | 1 108 372 | 6/2001 |
| WO | WO 97/02797 | 1/1997 |
| EP | 1 108 373 | 6/2001 |
| WO | 99/33421 | 7/1999 |
| EP | 1 110 463 | 6/2001 |
| WO | WO 01/03524 | 1/2001 |
| EP | 1 118 277 | 7/2001 |
| WO | 01/58401 | 8/2001 |
| EP | 1 125 571 | 8/2001 |
| WO | 01/61093 | 8/2001 |
| EP | 1 159 883 | 12/2001 |
| WO | 01/67900 | 9/2001 |
| EP | 1 166 730 | 1/2002 |
| WO | 01/87217 | 11/2001 |
| EP | 1 179 302 | 2/2002 |
| WO | 01/87218 | 11/2001 |
| EP | 1 184 012 | 3/2002 |
| WO | 01/87562 | 11/2001 |
| EP | 1 188 427 | 3/2002 |
| WO | 01/87753 | 11/2001 |
| FR | 1.276.791 | 10/1960 |
| WO | 01/88245 | 11/2001 |
| FR | 1.276.791 | 10/1961 |
| WO | 02/49565 | 6/2002 |
| GB | 238557 | 8/1926 |
| WO | 02/052967 | 7/2002 |
| GB | 307652 | 3/1929 |
| WO | WO 03/041625 A1 | 5/2003 |
| GB | 571098 | 8/1945 |
| WO | WO 03/057107 A1 | 7/2003 |
| GB | 620555 | 3/1949 |
| WO | WO 2004/073430 A2 | 9/2004 |
| GB | 701081 | 12/1953 |
| GB | 1 342 022 | 12/1973 |
| GB | 2 069 820 A | 9/1981 |
| GB | 2 112 268 | 7/1983 |

OTHER PUBLICATIONS

US 5,915,536, 06/1999, Alberts et al. (withdrawn)

* cited by examiner

DISPOSABLE BOXER BRIEF

BACKGROUND OF THE INVENTION

The present invention pertains to pants having a garment shell made of a stretchable material. More particularly, the present invention pertains to boxer briefs having a garment shell made of a stretchable material. The pants may be absorbent or non-absorbent.

Pant-like garments have numerous applications including disposable clothing, training pants, feminine care products, adult incontinence products, disposable swimwear, or the like. Pant-like disposable garments are typically three-dimensional products so that the product has a unitary waist opening and two leg openings. The wearer raises and lowers the garment to apply the product. Three-dimensional, boxer shorts-like or boxer brief products are particularly appealing because the boxer shorts look more like conventional articles of clothes.

Many disposable pants are formed as composite structures in which several components are combined to form a product specifically suited to its intended purpose. For example, disposable pants often include one or more absorbent materials intended to absorb various bodily exudates such as urine, menstrual fluid, bowel movement material, and/or sweat. Such products may include a liquid permeable bodyside liner and a liquid impermeable outer cover, and can include other materials and features such as elastic materials and containment structures.

However, many disposable pants can be aesthetically unappealing. Existing disposable absorbent pants can often be overly bulky and can often resemble disposable baby diapers. Various attempts have been made to provide disposable pants having an improved, more clothing-like appearance.

Furthermore, past consumer research has indicated that discretion is an important product attribute for many consumers, including enuretic children using disposable absorbent products. One component of discretion includes an underwear-like or garment-like appearance for the absorbent product the enuretic child is wearing. Currently, absorbent products available for enuretic children are very similar in appearance to absorbent products used for toilet training.

Thus, what is lacking and needed in the art are garment-like, aesthetically appealing boxer shorts or boxer briefs which provide discretion to the wearer.

SUMMARY OF THE INVENTION

In response to the above-referenced unfulfilled need in the art, new pants have been invented. The material for the garment shell of the pant is a stretchable material.

One embodiment of the pant includes: a garment shell comprising a stretchable material and including a middle panel, two leg panels, two leg openings and two inseams. In another embodiment of the invention, the middle panel comprises two separate panels. In another embodiment of the invention, the pant is made from a single panel and includes: a garment shell comprising a stretchable material, the garment shell including a front region, a back region, a crotch region, hanging legs and two leg openings, and first and second inseams, each inseam extending from the crotch region to one of the leg openings. At least a portion of each of the front region, the back region, the crotch region and the hanging legs include portions of the single panel. In each of these embodiments, the pant can include an absorbent structure either separate from, or integral with, the garment shell.

The present invention relates to a wide variety of absorbent and non-absorbent pants, including training pants, swim pants, diaper pants, incontinence garments, feminine care products, health care garments, apparel for institutional, industrial and consumer use, or other garments. Disposable absorbent pants are adapted to be worn adjacent the body of a wearer to absorb and contain various exudates discharged from the body.

BRIEF DESCRIPTION OF THE DRAWINGS

Various features and advantages of the invention will be better understood from the following detailed description taken in conjunction with the drawings, wherein.

DEFINITIONS

Figure 1:
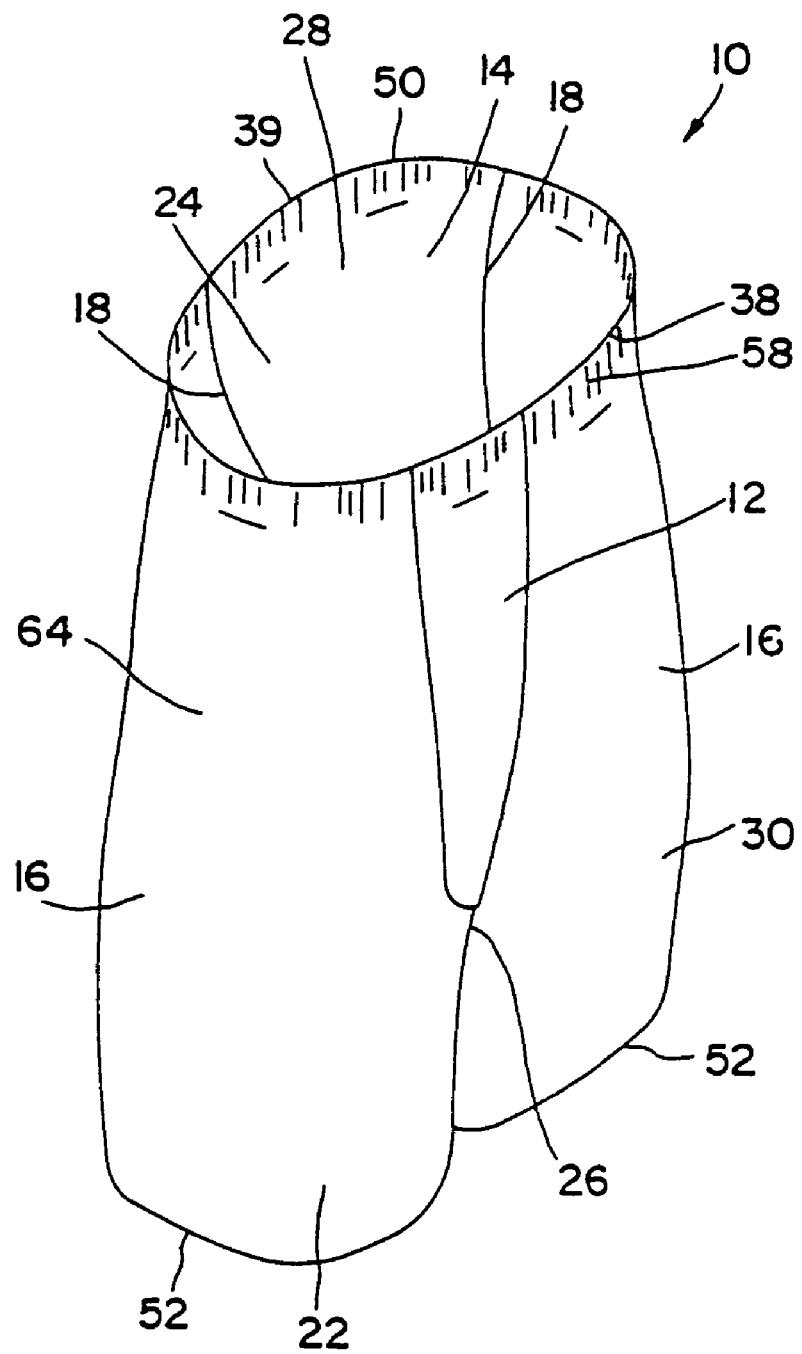
FIG. 1 is a perspective view of one embodiment of a pant according to the present invention.

Within the context of this specification, each term or phrase below will include the following meaning or meanings.

"Attached" refers to the joining, adhering, connecting, bonding, or the like, of two elements. Two elements will be considered to be attached together when they are attached directly to one another or indirectly to one another, such as when each is directly attached to intermediate elements.

"Biaxial stretch" refers to a material having stretchability in both longitudinal and lateral directions.

"Boxer shorts" refers to a pant, trunks, briefs, and the like that have leg structures which generally extend below the crotch toward the leg openings when worn.

"Boxer brief" is a pant, trunk or brief, or the like, that generally provides more form fitting properties than boxer shorts.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Enuretic" is used to refer to an individual with the condition of enuresis. Enuresis is the involuntary voiding of urine beyond the age of anticipated control. Nocturnal enuresis is commonly known as bedwetting.

"Fabrics" is used to refer to all woven, knitted and non-woven fibrous webs.

"Fastening component" refers to a hook or loop fastener as known in the art, but can also include other components used to fasten such as, adhesives, cohesirves, snaps, buttons and the like. "Fastening component," when used in the singular, can also include multiple components.

"Garment shell" refers to an outer cover or outer layer of a garment. In a single-ply garment, the single layer of the garment is the garment shell.

"Garment insert" refers to an inner layer of a garment. The garment insert provides a close-to-the-body fit about a wearer's lower torso, thereby serving as a form of built-in underwear within the garment.

"Hanging legs" refers to the portions of a garment which extend from the crotch region downward to the leg openings. "Downward" refers to a direction toward the ground when the garment is positioned on a standing wearer.

"Inseam" refers to a seam extending generally downward from the crotch region to approximately a leg opening of a pant-style garment substantially along the inner thigh of a standing wearer. The inseam can join two separate pieces of material, or can join separate edges of a single piece of material.

"Integral" is used to refer to various portions of a single unitary element rather than separate structures bonded to or placed with or placed near one another.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Member" when used in the singular can have the dual meaning of a single element or a plurality of elements.

"Nonwoven" and "nonwoven web" and "web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate (SBL)" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

The term "targeted elastic regions" or "targeted elastic zones" refers to isolated, often relatively narrow regions or zones in a single composite material or layer, which have greater elastic tension than adjacent or surrounding regions or zones, as described, for example, in U.S. patent application Ser. No. 09/855,189, filed on May 14, 2001 (U.S. Publication U.S. Ser. No. 2002/0002021, 03 Jan. 2002) by Raymond Jeffrey May et al. entitled "Targeted Elastic Laminate Having Zones of Different Basis Weights," and in U.S. patent application Ser. No. 09/855,188, filed on May 14, 2001 (U.S. Publication U.S. Ser. No. 2002/0009940, 24 Jan. 2002) by Raymond Jeffrey May et al. entitled "Targeted Elastic Laminate Having Zones of Different Polymer Materials," which are incorporated herein by reference.

The term "targeted elastic material" ("TEM") refers to a single elastic material or laminate having targeted elastic zones. TEM's include only materials or laminates which are made in a single manufacturing process, and which are capable of exhibiting targeted elastic properties without requiring an added elastic band or layer in the targeted elastic region. TEM's do not include materials having elasticized regions achieved through separate manufacture of an elastic band, and subsequent connection of the elastic band to the underlying material.

"Three-dimensional garment" refers to a garment that cannot be laid flat with all of its seams in one plane.

"Uniaxial stretch" refers to a material having strechability in either the longitudinal direction, or the lateral direction, but not both.

These terms may be defined with additional language in the remaining portions of the specification.

DESCRIPTION OF PREFERRED EMBODIMENTS

Figure 1A:
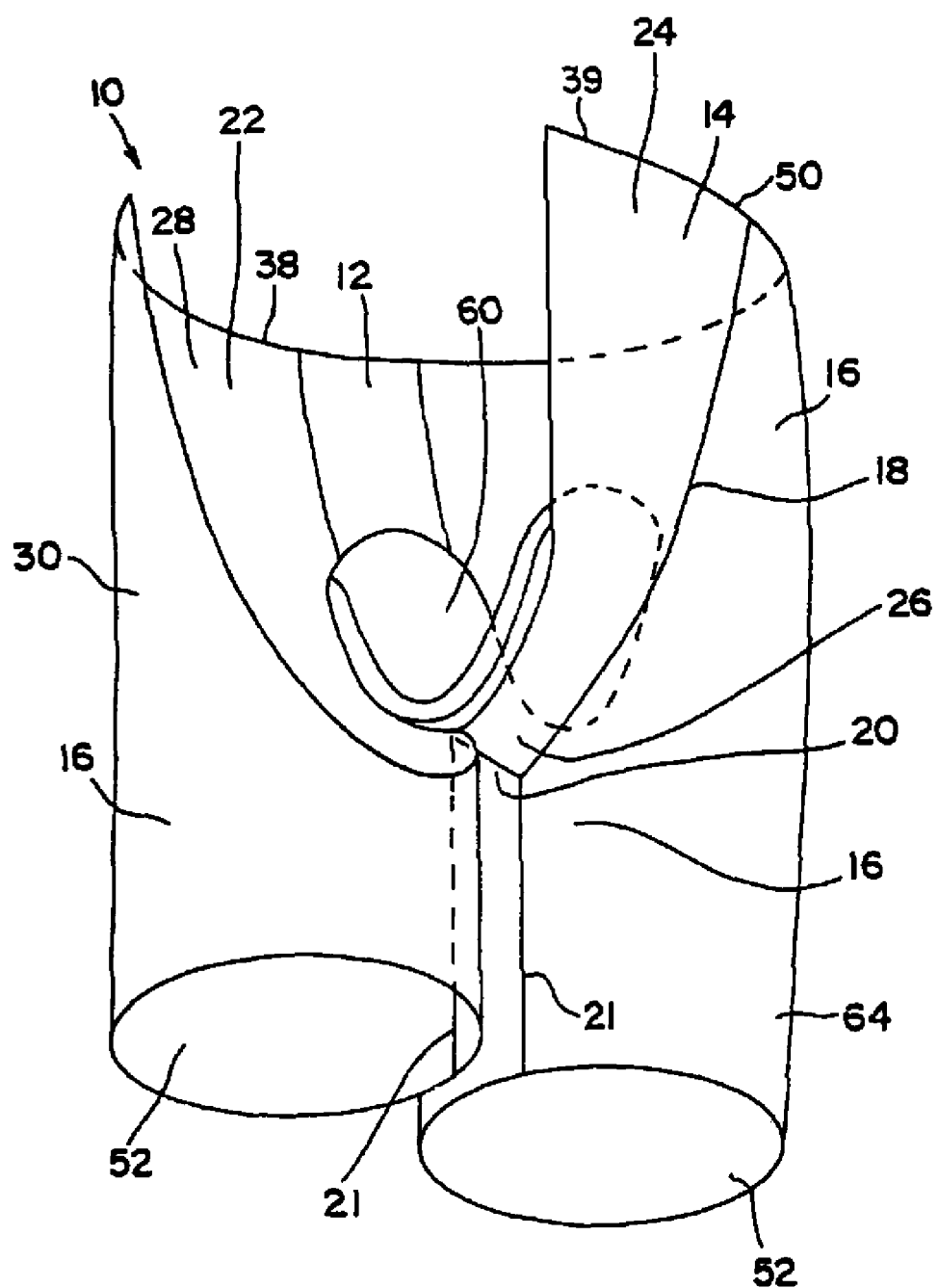
FIG. 1A is a cut-away view of the embodiment of FIG. 1 including an absorbent structure.
Figure 2:
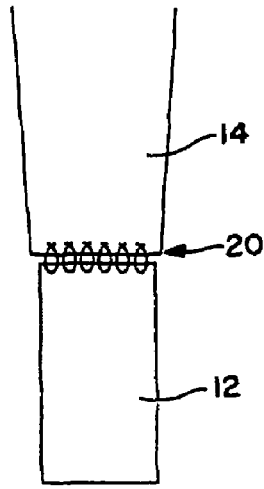
FIG. 2 is a plan view of the front panel and the back panel of the embodiment of FIG. 1.

As representatively illustrated in FIGS. 1 and 1A, an embodiment of a pant 10 of the present invention includes a garment shell 64 including four panels: a front panel 12, a back panel 14, and two leg panels 16. The garment shell 64 can include a front region 22, a back region 24, a crotch region 26, an inner surface 28 which is configured to contact the wearer, and an outer surface 30 opposite the inner surface 28 which is configured to face away from the surface of the wearer's body. The pant 10 also defines a pair of waist edges, which are designated front waist edge 38 and back waist edge 39. The front region 22 is contiguous with the front waist edge 38, and the back region 24 is contiguous with the back waist edge 39. The front region 22 includes the portion of the pant 10 which, when worn, is positioned on the front of the wearer while the back region 24 includes the portion of the pant 10 which, when worn, is positioned on the back of the wearer. The crotch region 26 of the pant 10 includes the portion of the pant which, when worn, is positioned between the legs of the wearer and covers the lower torso of the wearer.

Figure 3:
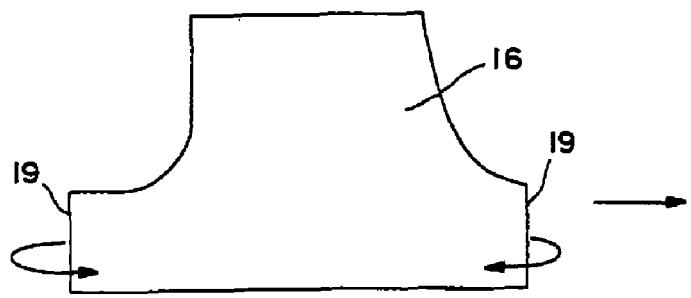
FIG. 3 is a plan view of a leg panel of the embodiment of FIG. 1.
Figure 4:
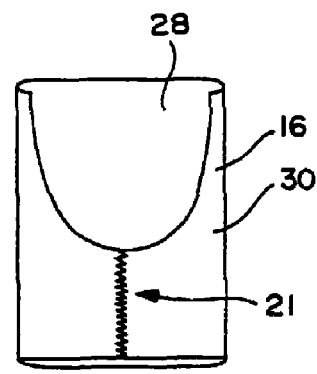
FIG. 4 is a side view of the leg panel of FIG. 3 showing an inseam.
Figure 5A:
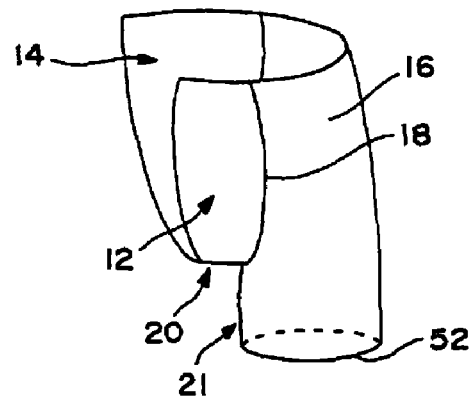
FIG. 5A is a partial front perspective view of the embodiment of FIG. 1 showing a front panel and a back panel attached to a leg panel.
Figure 5B:
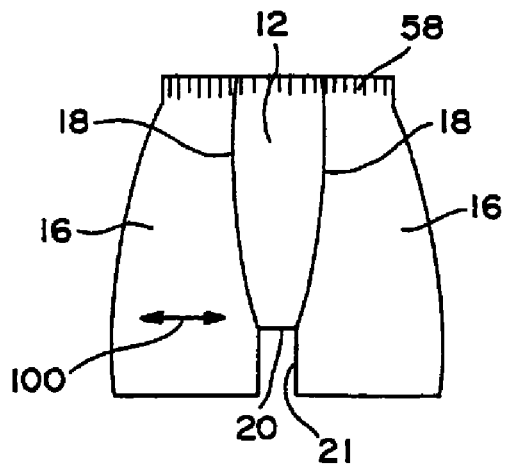
FIG. 5B is a front view of the embodiment of FIG. 1.
Figure 5C:
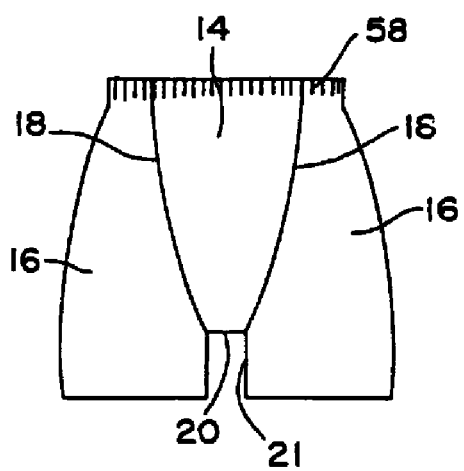
FIG. 5C is a back view of the embodiment of FIG. 1.

The front panel 12 and the back panel 14 can be attached together at crotch seam 20. (FIGS. 1A, 2 and 5A-5C) The front panel 12 and back panel 14 can be joined to each of the leg panels 16 at seam 18, and inseam edges 19 of each of the leg panels 16 (FIG. 3) are joined to each other at inseams 21 (FIGS. 1A and 4-5C) to define a three-dimensional pant configuration having a waist opening 50 and a pair of leg openings 52. The leg panels 16 define the leg openings 52. As is known in the art, seams 18, the crotch seam 20 and inseam 21 can be formed by adhesive, thermal and/or ultrasonic bonds, pressure bonds and also sewing and can be inward or outward fin seams or lap seams (not shown). The pant may also include an absorbent structure 60. (FIG. 1A).

Figure 6:
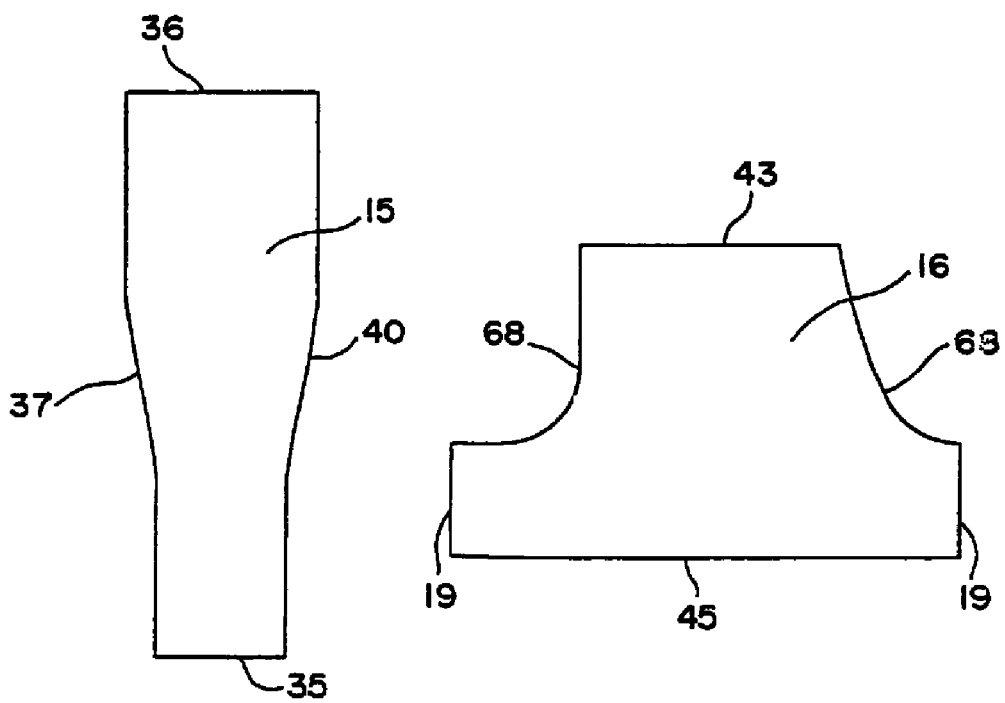
FIG. 6 is a plan view of a middle panel and a leg panel according to another embodiment of the present invention.
Figure 6A:
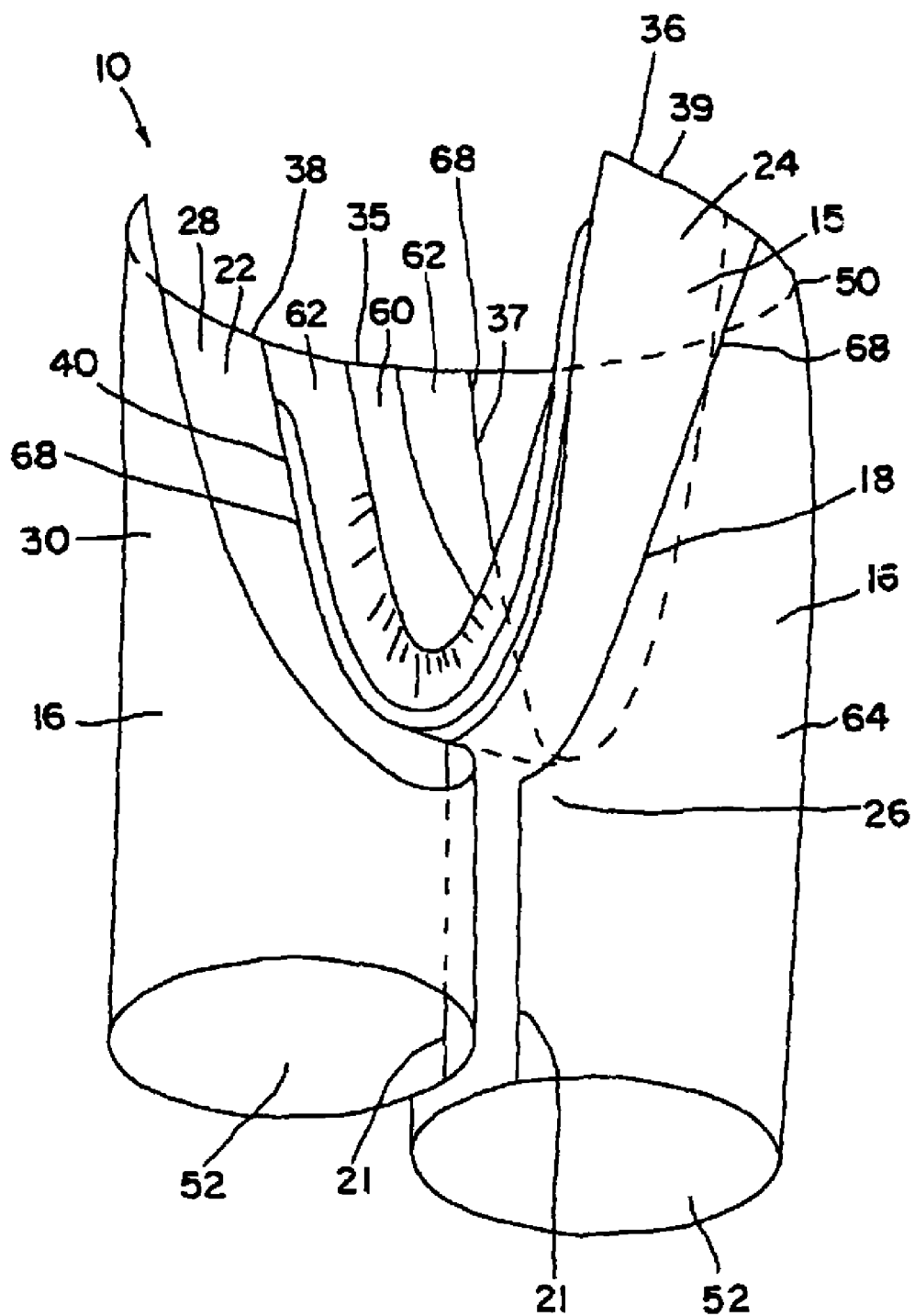
FIG. 6A is a cut-away view of the embodiment of FIG. 6 including an absorbent structure.

In particular embodiments, a single panel, namely, middle panel 15 replaces the front and back panels as shown in FIGS. 6 and 6A, so that the garment shell 64 of pant 10 includes three panels: a middle panel 15 and two leg panels 16. The middle panel 15 defines a pair of middle panel waist edges, which are designated middle panel first waist edge 35 and middle panel second waist edge 36.

The middle panel 15 also defines a pair of middle panel side edges, which are designated first middle panel side edge 37 and second middle panel side edge 40. Each of the leg panels 16 defines a leg panel top edge 43, a leg panel bottom edge 45, two inseam edges 19, and two leg panel side edges 68. Each of the middle panel side edges 37 and 40 can be attached to both side edges 68 of one leg panel 16 at seam 18. For example, the second middle panel side edge 40 can be attached to leg panel side edges 68 of one leg panel 16, and the first middle panel side edge 37 can be attached to leg panel side edges 68 of the other leg panel 16. (FIG. 6A). The leg panels 16 define the leg openings 52. For each leg panel 16, each inseam edge 19 can be joined the other inseam edge 19 on the same leg panel 16 to define inseam 21 (FIG. 6A) to define a three-dimensional pant configuration having a waist opening 50 and a pair of leg openings 52, and two inseams 21. As known in the art, seams 18 and inseams 21 can be formed by adhesive, thermal and/or ultrasonic bonds, pressure bonds and also sewing and can be inward or outward fin seams or lap seams (not shown). The pant may also include an absorbent structure 60 (FIG. 6A).

Figure 7:
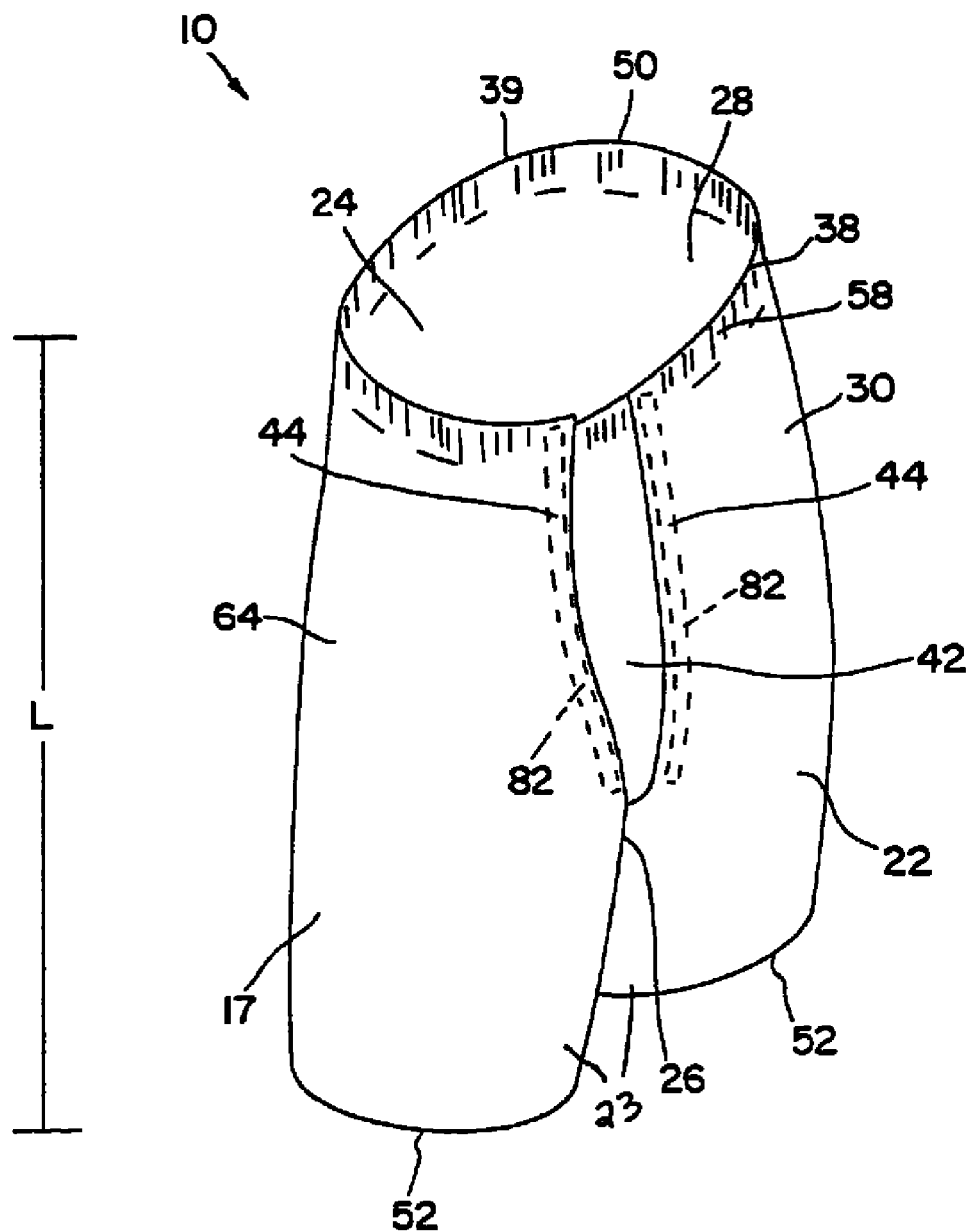
FIG. 7 is a perspective view of another embodiment of a pant according to the present invention.
Figure 7A:
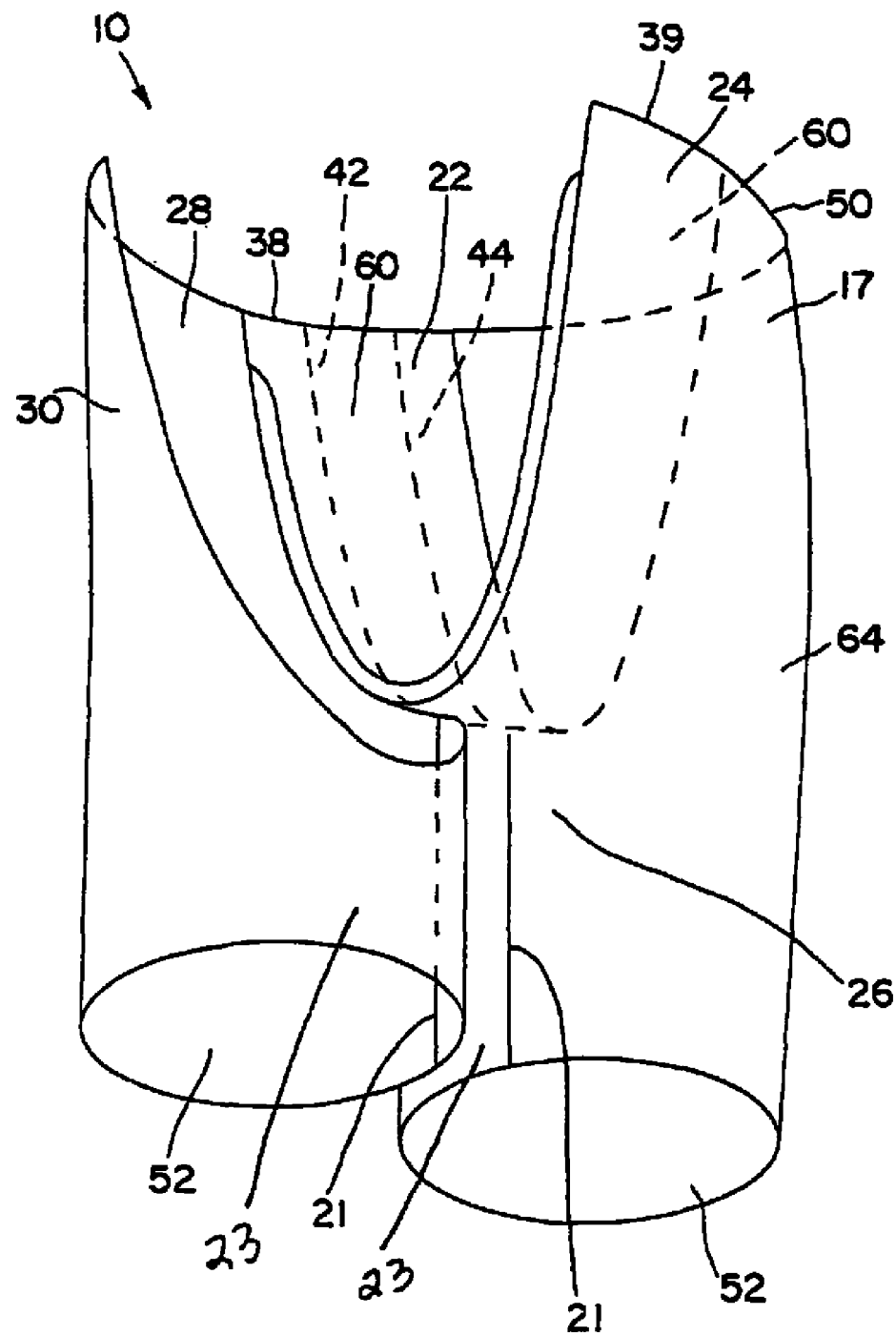
FIG. 7A is a cut-away view of the embodiment of FIG. 7 including an absorbent structure.

As representatively illustrated in FIG. 7, another embodiment of a pant 10 of the present invention includes a garment shell 64 including a single panel 17. The garment shell 64 can include a front region 22, a back region 24, a crotch region 26, an inner surface 28 and an outer surface 30, a front waist edge 38 and back waist edge 39. The garment shell 64 can also include hanging legs 23 which extend from the crotch region 26 downward to define leg openings 52 (FIGS. 7 and 7A). The pant can also include an absorbent structure 60. (FIG. 7A).

The panel 17 (FIGS. 8 and 9) has a dimension L which is about the desired length L of the pant 10 (FIG. 7). The panel 17 also has a width, shown as dimension W in FIG. 8. Dimension W can vary depending on the stretchability of the material used for panel 17, i.e., more stretchable materials require a smaller width W. The single panel 17 also has a first surface 25 and a second surface 27, which correspond to the inner surface 28 and outer surface 30, respectively, of the pant 10. In addition, the panel 17 has a top edge 70, a bottom edge 72, a first side edge 74 and a second side edge 76.

Figure 8:
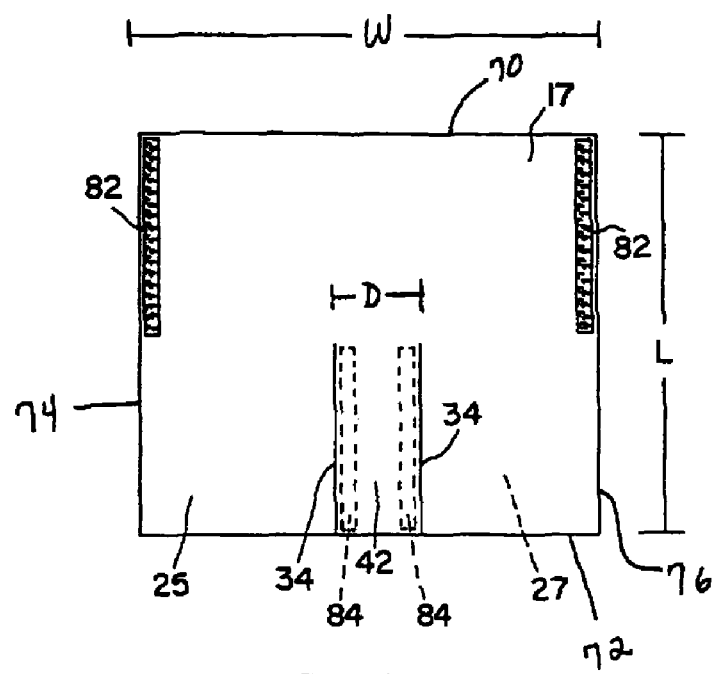
FIG. 8 is a plan view of the pant shown in FIG. 7, showing the side facing the wearer.

The panel 17 can further include slits 34 as shown in FIG. 8. The slits 34 can be made originating from the bottom edge 72 and extending toward top edge 70, for example, by a rotary die cutter, a reciprocating die cutter, a water cutter or a laser (not shown), or by any other method known in the art. The length of slits 34 can vary depending upon the desired length of inseams 21, with shorter slits 34 providing shorter inseams 21 (FIG. 7A). In particular embodiments, the length of each slit 34 can be up to about 90%, particularly about 50%, of the distance of the dimension L. The slits 34 are spaced apart by a distance D and define center flap portion 42 (FIG. 8). Distance D should be located substantially centered with respect to the width W of panel 17 and represents the width of center flap portion 42. Distance D will also vary depending on the stretchability of the material used for panel 17. In particular embodiments, dimension D can be in a range of about 10% to about 50% of the width W of panel 17.

The first surface 25 of panel 17 can include fastening components 82 that are adapted to refastenably connect to mating fastening components 84 located on the second surface 27 of panel 17. Fastening components 82 can be located on the first surface 25 so that the fastening components 82 abut the first and second side edges 74 and 76 of panel 17. In the alternative, the fastening components 82 can be spaced from the first and second side edges 74 and 76 at a distance up to about 25% of the width W of the panel 17. Mating fastening components 84 can be located on the second surface 27 at any location between the slits 34. The length of mating fastening components 84 is in particular embodiments substantially the same as the length of slits 34. Furthermore, the length of fastening components 82 is in particular embodiments substantially the same as the length of mating fastening components 84. The fastening components 82 and mating fastening components 84, as described below, serve to attach either the first surface 25 or the second surface 27 of the panel 17 to the center flap portion 42. Alternatively, any other attachment means known in the art can be used, for example, adhesive, thermal and/or ultrasonic bonds, pressure bonds and also sewing.

In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

Figure 9:
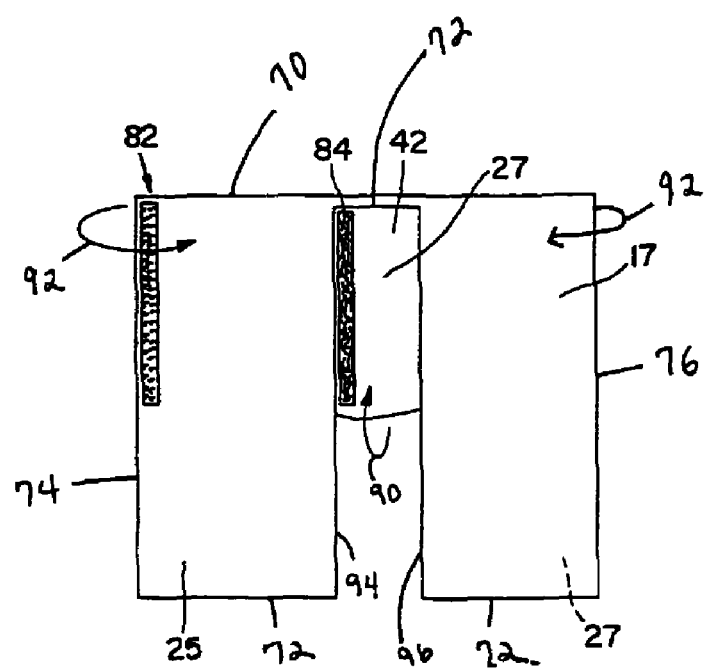
FIG. 9 is a front view of the pant shown in FIG. 8, showing a center flap portion folded up prior to formation of the seams.

The fastening components 82 can be located on the first surface 25 of panel 17 and the mating fastening components 84 can be located on the second surface 27 of the panel 17 as previously described and as shown in FIGS. 8 and 9. (The dotted lines indicate that the mating fastening component 84 is located on the opposite surface visible in the drawing.) Alternatively, the fastening components 82 can be located on the second surface 27 of the panel 17 and the mating fastening components 84 can be located on the first surface 25 of the panel 17. In such an embodiment, additional slits (not shown) originating at side edges 74 and 76 would be needed to accommodate superimposing fastening components 82 and mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 can be rectangular, although they can alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

After formation of the slits 34, the center flap portion 42 between slits 34 can be folded in the direction of arrow 90, as illustrated in FIG. 9, by any of various means, such as mechanical, hydraulic, or other methods known in the art, so that the bottom edge 72 of the center flap portion 42 is substantially aligned with the top edge 70 of the panel 17. The slits 34 also define a first center edge 94 and a second center edge 96. First and second side edges 74 and 76 are folded in the direction of arrows 92 by any of various means, such as an air blast, a folding board, a folding ski, or other methods known in the art, and the fastening components 82 and mating fastening components 84 are connected to form seams 44 (FIGS. 7 and 7A), to define a three-dimensional pant configuration having a waist opening 50, a pair of leg openings 52, hanging legs 23 and two inseams 21. As is known in the art, seams 44 and inseams 21 can be inward or outward fin seams (not shown) or lap seams. Inseams 21 can be formed by attaching the first center edge 94 to the lower portion of first side edge 74 and by attaching the second center edge 96 to the lower portion of second side edge 76 by adhesive and/or ultrasonic bonds, pressure bonds and also sewing. Furthermore, it is also contemplated that inseams 21 can be formed by the previously described fastening components and mating fastening components.

The invention is also directed to the method of making a pant including a single panel. The steps of the method correspond to the previously described and illustrated pant 10 with a single panel 17 and include: providing a single panel 17 comprising a top edge 70, a bottom edge 72, first and second side edges 74 and 76 and first and second surfaces 25 and 27, the single panel 17 defining a width W and a length L; making at least two slits 34 originating from the bottom edge 72 and extending toward the top edge 70, the at least two slits 34 defining a center flap portion 42, a first center edge 94 and a second center edge 96; folding the center flap portion 42 toward the top edge 70 of the single panel 17; attaching one of the first surface 25 and the second surface 27 of the single panel 17 to the center flap portion 42; attaching the first center edge 94 to the first side edge 74 to form the first inseam 21 and attaching the second center edge 96 to the second side edge 76 to form the second inseam 21. It is also contemplated that the pant 10 of this embodiment including a single panel 17 could be made by providing interconnected panels in the form of a web of material.

The pant 10 can also have a waist elastic member 58. The waist elastic member 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the waist elastic member 58 includes a plurality of dry-spun coalesced multifilament spandex elastomeric threads sold under the trade name LYCRA® and available from E.I. du Pont de Nemours and Company, Wilmington, Del., U.S.A. Alternatively, multiple strands of 310 decitex LYCRA® may be also laminated at 250% elongation between spunbond facings in addition to an adhesive. In particular embodiments, the elastic material includes a stretch-thermal laminate (STL), a neck-bonded laminated (NBL), a reversibly necked laminate, or a stretch-bonded laminate (SBL) material. Methods of making such STL, NBL and SBL materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the names of Taylor et al.; PCT Publication WO 01/88245 published on Nov. 22, 2001 in the names of Welch, et al.; all of which are incorporated herein by reference. Alternatively, the waist elastic member 58 can include other woven or nonwoven materials, such as stretchable but inelastic materials.

Alternatively, the waist elastic member 58 can be a targeted elastic zone integrated into the material of the garment shell 64. As another alternative, the waist elastic member 58 can be a "temporarily inhibited elastic." "Temporarily inhibited elastic" is described for example in U.S. Pat. No. 5,545,158 issued Aug. 13, 1996, to Jessup, U.S. Pat. No. 5,669,996 issued Sep. 23, 1997, to Jessup, and U.S. Pat. No. 5,500,063 issued Mar. 19, 1996, to Jessup, each of which is herein incorporated by reference, and references cited therein. As another alternative, the waist elastic member 58 can be a thermally-elasticizable strip described, for example, in U.S. Pat. No. 4,663,106 issued May 5, 1987 to Pomplun et al., herein incorporated by reference.

The garment shell 64 is desirably constructed of materials which are comfortable against the skin and non-irritating. It is contemplated that the garment shell 64 can be either disposable or durable, in the embodiments without an absorbent structure, and disposable in the embodiments with an absorbent structure. Both nonwoven and woven materials are contemplated for the garment shell 64. For example, the garment shell 64 for pant 10 can be selected from a wide variety of materials, including elastic, stretchable, or nonstretchable materials. The garment shell 64 can be a single layer of material or a multi-layered laminate structure. Suitable materials for the garment shell 64 include stretchable nonwovens, and nonwoven laminates. Nonstretchable nonwovens are also contemplated.

Materials suitable for the garment shell 64 include elastomeric materials, in the form of strands, film, and/or foam, including diblock, triblock, tetrablock, or other multi-block elastomeric copolymers such as olefinic copolymers, including styrene-isoprene-styrene, styrene-butadiene-styrene, styrene-ethylene/butylene-styrene, or styrene-ethylene/propylene-styrene, which may be obtained from Kraton Polymers, Belpre, Ohio, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cubic centimeter, available from Dow Chemical Co. under the trade name AFFINITY®.

A number of block copolymers can also be used to prepare the elastomeric material for the garment shell 64. Such block copolymers generally include an elastomeric midblock portion B and a thermoplastic endblock portion A. The block copolymers may also be thermoplastic in the sense that they can be melted, formed, and resolidified several times with little or no change in physical properties (assuming a minimum of oxidative degradation). Alternatively, the elastic component can be made of a polymer that is not thermally processable, such as LYCRA® spandex, available from E. I. Du Pont de Nemours Co., or cross-linked natural rubber in film or fiber form. Thermoset polymers and polymers such as spandex, unlike the thermoplastic polymers, once cross-linked cannot be thermally processed, but can be obtained on a spool or other form and can be stretched and applied as strands in the same manner as thermoplastic polymers. As another alternative, the elastomeric material can be made of a thermoset polymer, such as AFFINITY®, available from Dow Chemical Co., that can be processed like a thermoplastic, i.e. stretched and applied, and then treated with radiation, such as electron beam radiation, gamma radiation, or UV radiation to cross-link the polymer, or use polymers that have functionality built into them such that they can be moisture-cured to cross-link the polymer, thus resulting in a polymer and the enhanced mechanical properties of a thermoset.

Endblock portion A may include a poly(vinylarene), such as polystyrene. Midblock portion B may include a substantially amorphous polyolefin such as polyisoprene, ethylene/propylene polymers, ethylene/butylenes polymers, polybutadiene, and the like, or mixtures thereof.

Suitable useful block copolymers include at least two substantially polystyrene endblock portions and at least one substantially ethylene/butylenes mid-block portion. A commercially available example of such a linear block copolymer is available from Kraton Polymers under the trade designation KRATON® G1657 elastomeric resin. Another suitable elastomer is KRATON® G2760 available from Kraton Polymers.

The garment shell 64 may also contain blends of elastic and inelastic polymers, or of two or more elastic polymers, provided that the blend exhibits stretchable properties. In particular embodiments, the material for the garment shell 64 includes the previously described stretch-thermal laminate (STL), a neck-bonded laminated (NBL), a reversibly necked laminate, or a stretch-bonded laminate (SBL) material.

The material for the garment shell 64 should have at least uniaxial stretch properties, and desirably biaxial stretch properties. In those embodiments having uniaxial stretch properties, the direction of stretch on the finished pant 10 can be left to right on the wearer, for example, shown by arrow 100 in FIG. 5B.

In particular embodiments, the material for the garment shell 64 can include a targeted elastic material. In these embodiments, the targeted elastic zones of the targeted elastic material should be aligned so that the targeted elastic zones in the finished garment are oriented circumferentially on the wearer.

The garment shell 64 may also be made of those materials of which the absorbent structure 60 (described below) is made. It is desired that the garment shell 64 provides a relatively cloth-like texture to the wearer.

Figure 10:
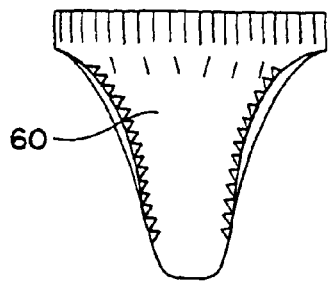
FIG. 10 is a front view of one embodiment of an absorbent structure used in the pant of the present invention.
Figure 11:
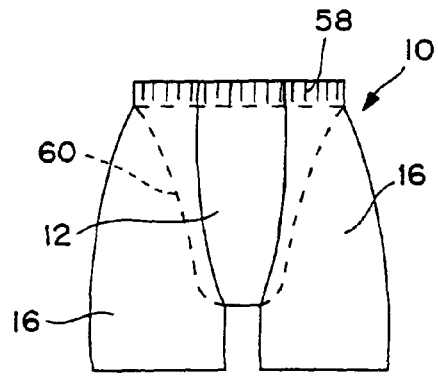
FIG. 11 is a front view of the embodiment of FIG. 1 including an absorbent structure.
Figure 12:
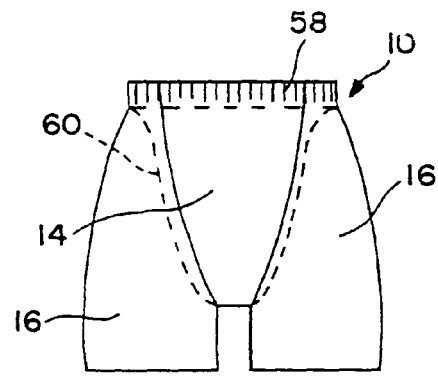
FIG. 12 is a back view of the embodiment of FIG. 1 including an absorbent structure.
Figure 13:
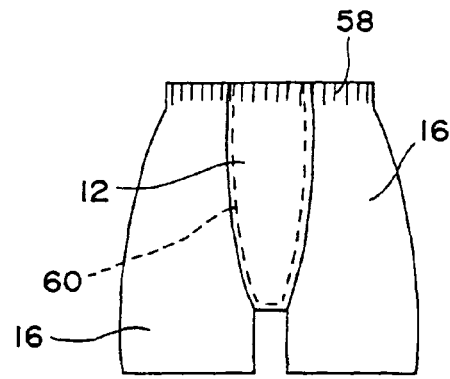
FIG. 13 is a front view of the embodiment of FIG. 1 including an absorbent structure integral with the garment shell.
Figure 14:
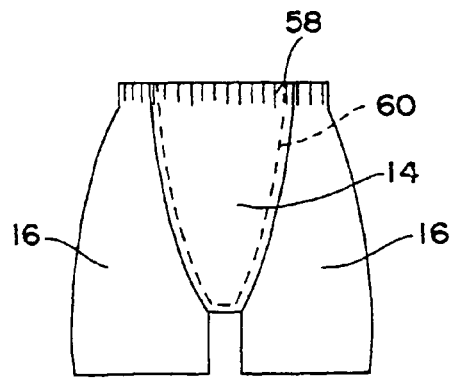
FIG. 14 is a back view of the embodiment of FIG. 1 including an absorbent structure integral with the garment shell.

The pant 10 can also include an absorbent structure 60. (FIGS. 1A, 6A, 7A and 10-14). The absorbent structure 60 can be attached to the garment shell 64 at the front waist edge 38 and back waist edge 39, or at some point below the front waist edge 38 and back waist edge 39 on the front region 22 and back region 24. Alternatively, the absorbent structure 60 can be attached to the garment shell 64 in the crotch region 26. As another alternative, the absorbent structure can be integral with the garment shell 64 as shown in FIGS. 13-14 or can be a separate structure as shown in FIG. 10.

Any suitable absorbent structure can be used for the absorbent structure 60. The absorbent structure 60 can be any structure which is generally compressible, conformable, non-irritating to the skin, and capable of absorbing and retaining liquids and certain body wastes. The absorbent structure 60 can be manufactured in a wide variety of sizes and shapes, from a wide variety of liquid absorbent materials commonly used in the art, and may be stretchable, non-stretchable, or elastic. For example, the absorbent structure 60 can suitably include a matrix of hydrophilic fibers, such as a web of cellulosic fluff, mixed with particles of a high-absorbency material commonly known as superabsorbent material. In a particular embodiment, the absorbent structure 60 includes a matrix of cellulosic fluff, such as wood pulp fluff, and superabsorbent hydrogel-forming particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 60 to better contain and absorb body exudates. The concentration of the superabsorbent particles can also vary through the thickness of the absorbent structure 60. Alternatively, the absorbent structure 60 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent structure 60 includes a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent structure 60 in an amount of from 0 to about 90 weight percent based on total weight of the absorbent assembly. The absorbent structure 60 suitably has a density within the range of about 0.10 to about 0.35 grams per cubic centimeter. The absorbent structure 60 may or may not be wrapped or encompassed by a suitable wrap that may help maintain the integrity and/or shape of the absorbent assembly.

The absorbent structure 60 can also incorporate other materials that are designed primarily to receive, temporarily store, and/or transport liquid along the mutually facing surface with absorbent structure 60, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C. U.S.A.

In particular embodiments, the absorbent structure 60 is thin to provide a slim, comfortable, non-bulky pant 10. Any suitable thin absorbent structure may be used, such as for example, the thin absorbent described in WO 02/49565, published Jun. 27, 2002, by Sawyer et al., which is incorporated herein by reference.

The absorbent structure 60, desirably although not necessarily, includes a pair of containment flaps 62 (FIG. 6A) which are configured to provide a barrier to the transverse flow of body exudates. A flap elastic member (not shown) can be operatively joined with each containment flap in any suitable manner as is well known in the art. The elasticized containment flaps define an unattached edge which assumes an upright, generally perpendicular configuration in at least the crotch region 26 of the pant 10 to form a seal against the wearer's body. Suitable constructions and arrangements for the containment flaps are generally well known to those skilled in the art and are described in U.S. Pat. No. 4,704,116 issued Nov. 3, 1987 to Enloe, which is incorporated herein by reference.

In the alternative, a pant-like garment insert could be used for the absorbent structure 60. For example, the pant-like garment insert suitably includes a body side liner, an outer cover, an absorbent assembly between the body side liner and the outer cover, and side panels. Examples of suitable inserts include a training pant, such as HUGGIES® PULL-UPS® Disposable Training Pants and disposable underpants, such as GOODNIGHTS® Disposable Underpants both manufactured by Kimberly-Clark Corporation, Neenah, Wis., U.S.A.

As another alternative, a pad-type absorbent could be used for the absorbent structure. The pad-type absorbent can be attached in the crotch region 26 of the pant 10. An example of a suitable pad-type absorbent is a feminine care pad such as KOTEX® Feminine Napkins, KOTEX® LIGHTDAYS® Pantiliners, or an incontinence absorbent pad such as POISE® Feminine Guards and Pads or DEPEND® Guards for Men, all manufactured by Kimberly-Clark Corporation, Neenah, Wis., U.S.A.

One suitable example of an absorbent structure 60 is illustrated in FIG. 10. Such an absorbent structure can be described, for example, as a belt-style or mini-brief style undergarment. FIGS. 11-12 are front and back views, respectively, of a four panel embodiment of pant 10 including such an absorbent structure 60.

The absorbent structure 60 can be introduced into the pant 10 by being attached to the garment shell 64 in any suitable manner known in the art at any point in the manufacturing process. In particular embodiments, the absorbent structure 60 can be placed on top of the crotch seam 20 in a four panel embodiment, or on top of the middle panel 15 in a three panel embodiment, or on top of the garment shell 64 in a one panel embodiment. As previously mentioned, the absorbent structure 60 can be attached to the pant 10 at the front waist edge 38 and back waist edge 39, or at some point below the front waist edge 38 and back waist edge 39 on the front region 22 and back region 24. The attachment of the absorbent structure 60 can be accomplished by ultrasonic, thermal or adhesive bonding, or any other suitable method known in the art. It is also contemplated that the attachment of the absorbent structure 60 can be accomplished by the previously described fastening components and mating fastening components, for example, by hook and loop fasteners. Attachment by fastening components and mating fastening components provides the ability to remove and discard the absorbent structure when soiled and retain the garment shell for subsequent use. In particular embodiments, the absorbent structure 60 is stretchable in order to provide the desired close to the body fit for the absorbent structure 60.

As previously mentioned, in particular embodiments, the pant 10 can have an absorbent structure integral with the garment shell 64. In particular embodiments, the pant 10 includes absorbent panels integral with the front panel 12 and/or the back panel 14 in a four panel embodiment, or integral with the middle panel 15 in a three panel embodiment (not shown) or integral with center flap portion 42 in the single panel embodiment (not shown). For example, as representatively illustrated in FIGS. 13 and 14, the absorbent structure 60 can be integral with either the front panel 12 or the back panel 14, or both, in a four panel embodiment.

In those embodiments of the pant 10 manufactured without an absorbent structure 60, it is contemplated that the pant 10 can be launderable and packaged together with a separate absorbent structure, such as, for example, a training pant. Alternatively, an absorbent structure could be purchased separately, such as previously mentioned, a training pant, such as HUGGIES® PULL-UPS® Disposable Training Pants, or disposable underpants, such as GOODNIGHTS® Disposable Underpants.

The various components of the pant can be connected together by any means known to those skilled in the art such as, for example, adhesive, thermal and/or ultrasonic bonds, and also sewing and other methods used in durable garment manufacturing. Desirably, most of the components are connected using ultrasonic bonding for improved manufacturing efficiency and reduced raw material costs. For example, in particular embodiments, the crotch seam 20 and the inseams 21 are made using ultrasonic bonding. Certain garment manufacturing equipment which is readily known and understood in the art, including frames and mounting structures, ultrasonic and adhesive bonding devices, transport conveyors, transfer rolls, guide rolls, tension rolls, and the like, have not been shown in the Figures.

It is contemplated that the pant of the present invention can be adapted to accommodate a range of fit styles such as a lower cut near the waist ("hip hugger"), a higher cut near the leg ("short shorts"), brief style and also long leggings style.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A disposable pant comprising:
    a garment shell including a stretchable middle panel and two stretchable leg panels, the middle panel attached to the leg panels along a continuous seam running from an upper edge of a front waist edge to an upper edge of a back waist edge, the leg panels defining two leg openings, and first and second inseams, each inseam extending from a crotch region to one of the leg openings;
    an absorbent structure in the crotch region of the garment shell; and
    wherein the disposable pant includes an inner surface configured to contact the wearer's body and an outer surface configured to face away from the wearer's body, the absorbent structure defining at least a portion of the inner surface.

2. The disposable pant of claim 1, further comprising a waist elastic extending along at least a portion of at least one of a front waist edge and a back waist edge of the garment shell.

3. The disposable pant of claim 1, wherein the middle panel comprises two separate panels attached at a crotch seam.

4. The disposable pant of claim 1, wherein the absorbent structure is attached to the garment shell.

5. The disposable pant of claim 1, wherein the absorbent structure is integral with the middle panel.

6. The disposable pant of claim 4, wherein the absorbent structure is attached to the garment shell with a fastening component.

7. The disposable pant of claim 4, wherein the absorbent structure comprises a stretchable material.

8. The disposable pant of claim 1, wherein at least one of the group consisting of the stretchable middle panel and the two stretchable leg panels comprises a targeted elastic material.

9. A disposable pant comprising a garment shell, the garment shell comprising:
    a stretchable middle panel having a middle panel first waist edge, a middle panel second waist edge and first and second middle panel side edges; and
    first and second stretchable leg panels, the leg panels each defining a leg opening and each having a leg panel top edge and a leg panel bottom edge, first and second inseam edges, and two leg panel side edges, the first inseam edge of the first leg panel joined to the second inseam edge of the first leg panel to define a first inseam, the first inseam edge of the second leg panel joined to the second inseam edge of the second leg panel to define a second inseam;
    the first middle panel side edge attached to the leg panel side edges of one leg panel and the second middle panel side edge attached to the leg panel side edges of the other leg panel along a continuous seam running from the middle panel first waist edge to the middle panel second waist edge;
    the disposable pant further comprising an absorbent structure in a crotch region of the disposable pant; and
    wherein the disposable pant includes an inner surface configured to contact the wearer's body and an outer surface configured to face away from the wearer's body, the absorbent structure defining at least a portion of the inner surface.

10. The disposable pant of claim 9, wherein the middle panel comprises two separate panels.

11. A disposable pant, comprising:
    a garment shell including a stretchable middle panel and two stretchable leg panels, the middle panel consisting of not more than two panels, attached to the leg panels along a continuous seam running from an upper edge of a front waist edge to an upper edge of a back waist edge, the leg panels defining two leg openings, and first and second inseams, each inseam extending from a crotch region to one of the leg openings.

12. The disposable pant of claim 11, further comprising a waist elastic extending along at least a portion of at least one of a front waist edge and a back waist edge of the garment shell.

13. The disposable pant of claim 11, further comprising an absorbent structure attached to the garment shell.

14. The disposable pant of claim 11, further comprising an absorbent structure integral with the garment shell.

15. The disposable pant of claim 13, wherein the absorbent structure is attached to the garment shell with a fastening component.

16. The disposable pant of claim 13, wherein the absorbent structure comprises a stretchable material.

17. The disposable pant of claim 11, wherein at least one of the group consisting of the stretchable middle panel and the two stretchable leg panels comprises a targeted elastic material.

* * * * *